United States Patent
Sampson et al.

(10) Patent No.: US 6,664,793 B1
(45) Date of Patent: Dec. 16, 2003

(54) FLUID PRESENCE AND QUALITATIVE MEASUREMENTS BY TRANSIENT IMMITIVITY RESPONSE

(76) Inventors: Allen R. Sampson, 317 N. 4th St., St. Charles, IL (US) 60174; Robert E. Davis, 125 Hillcrest, Hinsdale, IL (US) 60521

( * ) Notice: Subject to any disclaimer, the term of this patent is extended or adjusted under 35 U.S.C. 154(b) by 0 days.

(21) Appl. No.: 10/087,281

(22) Filed: Mar. 1, 2002

(51) Int. Cl.$^7$ ............................................. G01N 27/02
(52) U.S. Cl. ............................ 324/439; 324/444
(58) Field of Search ................................. 324/439, 441, 324/442, 444, 446, 450, 676, 710, 663, 693, 71.1; 205/787; 73/53.05

(56) References Cited

U.S. PATENT DOCUMENTS

| | | | |
|---|---|---|---|
| 3,584,297 A | 6/1971 | Koski | 324/611 |
| 4,132,944 A | 1/1979 | Bentz | 324/441 |
| 4,516,077 A | 5/1985 | Fenneman et al. | 324/425 |
| 4,634,982 A | 1/1987 | Pungor et al. | 324/448 |
| 5,270,663 A * | 12/1993 | Sano et al. | 324/676 |
| 5,497,753 A | 3/1996 | Kopera | 123/494 |
| 5,507,178 A | 4/1996 | Dam | 73/61.49 |
| 5,543,717 A * | 8/1996 | Kordas | 324/444 |
| 5,612,622 A * | 3/1997 | Goldman et al. | 324/444 |
| 6,084,417 A | 7/2000 | Berberich | |
| 6,169,394 B1 | 1/2001 | Frazier et al. | 324/71.4 |
| 6,232,783 B1 | 5/2001 | Merrill | 324/439 |

* cited by examiner

Primary Examiner—John E. Chapman
Assistant Examiner—James Kerveros
(74) Attorney, Agent, or Firm—Godfrey & Kahn, S.C.

(57) ABSTRACT

An apparatus and method for obtaining a measurement of various qualities of an electrochemical cell. The apparatus includes first and second electrodes and an excitation source for providing a time varying excitation voltage to the first electrode. The excitation voltage is switched between two voltage levels with the first and second voltages alternately applied to the first electrode for predetermined times. An external capacitance is connected between the second electrode and ground. The apparatus is capable of determining the time related rates at which electrical charge is transferred from the first electrode to charge the external capacitance. These rates, here termed Transient Immitivity Response (TIR), may be provided as a digital or analog output.

26 Claims, 14 Drawing Sheets

Fig. 1
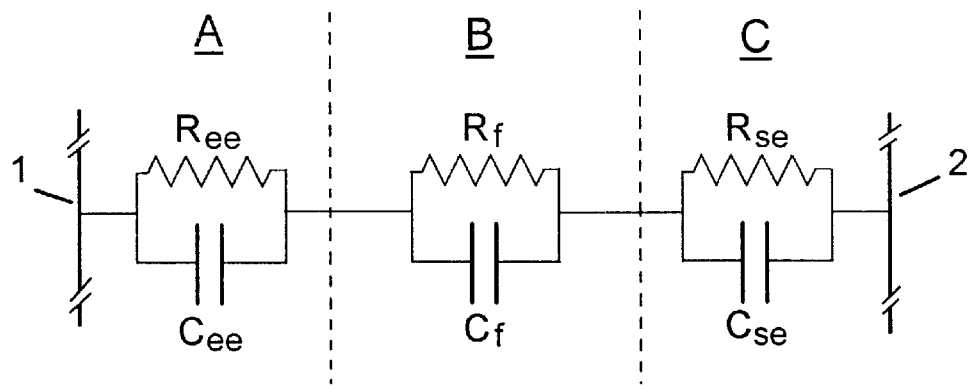
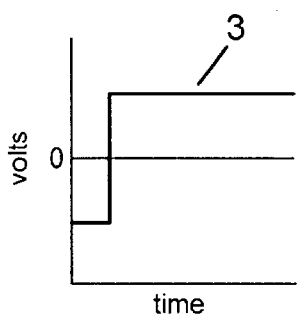
Fig. 2A
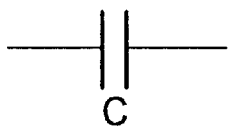
Fig. 2B
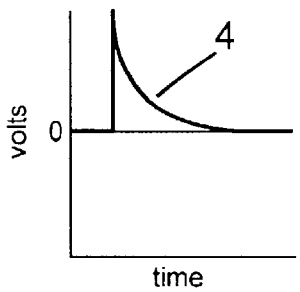
Fig. 2C
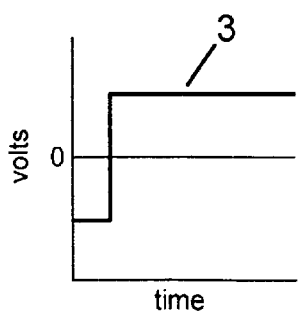
Fig. 3A
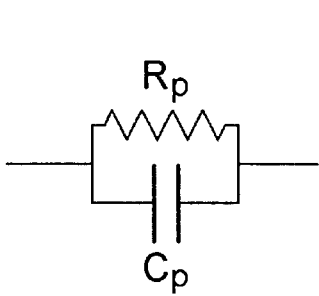
Fig. 3B
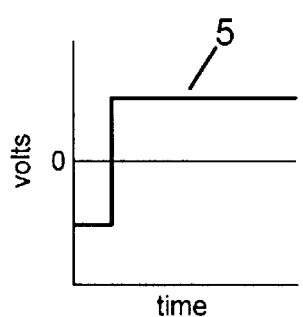
Fig. 3C Present Invention Resistance Capacitance Intrinsic Time Constant Present Invention Resistance Capacitance Intrinsic Time Constant Present Invention Resistance Capacitance Intrinsic Time Constant

FLUID PRESENCE AND QUALITATIVE MEASUREMENTS BY TRANSIENT IMMITIVITY RESPONSE

FIELD OF THE INVENTION

The present invention relates to a process for measuring the presence and various qualities of fluids, and materials containing fluids. More specifically, the present invention describes a process for detecting minute compositional changes in single sampling or continuous flow monitoring of fluids which offers extreme sensitivity, simplified temperature compensation, probe design, materials and control electronics.

BACKGROUND OF THE INVENTION

A myriad of fluids are used in many scientific and industrial processes, as well as in end user applications. Initial, in-process and in-use testing of these fluids can often help prevent potential problems. Many processes rely on precise mixtures of fluids, slurries, suspensions or wetted materials and require accurate feedback on the resultant mixtures. End users often depend on accurate compositions of fluids, slurries, suspensions or wetted materials for safe and efficient use. Qualitative measurement of these materials can often prevent costly mistakes, damage or injury.

Electronic analysis of fluid compositions has historically been complicated by the fact that generally any such fluid has a dielectric constant, conductance and double-layer effects, each of which produces complex electrical responses. While measurements of these qualities are commonplace, they are plagued with instrumental difficulties such as probe design, erratic temperature dependencies and complex control electronics in the effort to get accurate and sensitive results.

In-use or in-process controls often require sensors capable of properly handling varying levels of flow, pressure and temperature while accurately measuring compositional changes. Current methods of measuring the dielectric constant or conductance of a fluid require either a very small range of variance in any of these effects, or extreme and technically complex compensations for them.

The dielectric constant of fluids is a common qualitative measure associated with fluids. It is known that the dielectric constant in solids is a measure of the ability of molecules to polarize or shift their internal charges in response to external fields. In fluids, the molecules Are also able to move about, rotating to orient in a field and/or migrating within the fluid. In electronic terms, the dielectric constant is the analog of a capacitor.

Many patents exist that are directed to measuring the capacitance of fluids. U.S. Pat. Nos. 4,132,944, 5,497,753 and 5,507,178 are representative of capacitance-measuring techniques.

Conductivity (the reciprocal of electrical resistance) is another common measure used to produce a qualitative indication of fluid compositions and charged species in a fluid. Charged species, or ions, present in a fluid provide a means for the passage of electrons through a fluid. The more ions present, the lower the electrical resistance of the fluid and the greater the magnitude of current that can flow through the fluid. In electronic terms this phenomenon is the analog of a resistance.

Numerous patents have been directed to fluid conductivity measurements, including U.S. Pat. Nos. 4,132,944, 4,634,982, 6,169,394 and 6,232,783, all representative of conductivity based applications.

Both of the above-described measures are greatly affected by temperature and other influences. In many cases, the precise theory behind these wide variances is not directly known or reliably predicted and varies considerably dependent on composition.

Measurements of conductivity and dielectric properties together have been performed in the past in efforts to simplify and solve many of the problems highlighted above. U.S. Pat. Nos. 4,516,077 and 6,169,394 are representative of this approach. In the latter patent, complex measurements were made of the electrical impedance of a fluid (i.e., the effect of a parallel resistance and capacitance). Unfortunately, this invention used complex electronics in generating a wide range of excitation frequencies, while-variances such as temperature dependencies were not addressed.

In U.S. Pat. No. 4,516,077, a sensor is described which is useful in a limited number of solvent solutions including water, alcohols and glycols. This invention included a method of electronically charging a fluid, disconnecting the charging means, and then measuring the time necessary for the charge across the fluid to dissipate (termed the "intrinsic time constant"). This invention essentially measures the re-diffusion rate of the polarization and electrical charges as they return to equilibrium devoid of any external electrical influences and is greatly affected by temperature and fluid flow rates.

The measurement of any fluid quality is complicated by the electrode-fluid interface. Each such interface includes its own resistance and capacitance, which are known to often be larger than those of the fluid itself. Electrochemical reactions caused by the introduction of an electrical current into a fluid can cause electrode corrosion and contamination. Sensed voltages or currents often need amplification and signal conditioning to provide suitable readings. These, and other problems, have seldom been addressed in previous inventions.

Therefore, it is desirable to develop an invention that uses the electrical qualities of the fluid to provide the primary measure while avoiding the above-described complications.

BRIEF SUMMARY OF THE INVENTION

The present invention relates to a process for measuring the presence and various qualities of fluids and materials containing fluids. It offers improved performance over previous methods in its range and sensitivity, as well as relative insensitivity to temperature and fluid flow. In addition, this process offers simplified design and measurement.

The present invention includes a process and an apparatus for controlling and measuring various electrochemical effects of simplified electrochemical cells. However, the underlying effects measured are complex in nature. The present invention controls some of the individual influences of those effects to derive a measurement that has advantages over previous techniques and is termed here Transient Immitivity Response (TIR).

The primary feature of the invention is the use of a capacitance external to the cell to accumulate, control and limit the electrical currents passing through the cell. Transient immitivity response refers to the interactions between this capacitance and the current transfer mechanisms within the electrochemical cell. These interactions create a complex rate of electrical charging and discharging of this external capacitance that can be measured in many different ways.

This capacitance, the cell configuration and other external components may be adjusted to enhance or reduce the effect of various charge transfer mechanisms and to fit the invention to virtually any fluid. The transient immitivity response is the time related complex rate at which charge is passed through the cell and accumulated on the external capacitance.

One embodiment according to the invention includes two electrodes spaced apart from each other and both in contact with a fluid-being tested. This embodiment includes an excitation source for providing a time-varying excitation voltage to a first one of the electrodes. The excitation voltage is switched between a first defined voltage level and a distinct second defined voltage level. The first and second voltage levels are alternatively applied to the first electrode for specific time periods. This source has a low source resistance such that it is able to supply sufficient electrical current to change the first electrode's electrical potential in a minimal time and thereby rapidly charge the first electrode's capacitance.

According to the invention, a defined capacitance is located between the second electrode and an electrical or circuit ground. The ground has a defined voltage. This embodiment also includes a voltage detector for detecting a sensed voltage induced on the defined capacitance. The sensed voltage is proportional to electrical charges conducted through the fluid from the first electrode to the second electrode as a consequence of the excitation voltage applied to the first electrode. This voltage detector has a very high resistance to electrical ground such that there is no substantial current flow through it from the cell. Examples of suitable voltage detectors include current generation FET transistors, op amps and CMOS logic circuits having input resistances greater then $10^{11}$ ohms.

In this embodiment, the voltage level at the excitation source is held constant at least until the cell is at equilibrium when a fluid is present. If there is no fluid present, no voltage will be detected at the sensing or detecting means. If a fluid is present at equilibrium, all portions of the electrochemical cell of the embodiment will be at essentially the same voltage as the excitation voltage and the voltage sensed at the second electrode will be essentially equal to the voltage at the first electrode. The excitation voltage of the first means is then switched to a second voltage level. The cell will now work to come to equilibrium at this second voltage level.

The embodiment further includes a means for determining one or more time intervals between the switch in first and second defined voltage levels and when a sensed voltage at the capacitance attains one or more selected voltage levels. These time intervals represent the transient immitivity response of the fluid. Alternately, this means may measure the voltage attained at the capacitance at one or more predetermined time intervals after the switch in first and second defined voltage levels. Once again, providing a measure of the Δvoltage/Δtime nature of the transient immitivity response. The voltage level attained at the second electrode is a time-related function of all of the resistances and capacitances of the electrode interface and the fluid, and the change in voltage of the first excitation source. This embodiment is further capable of providing the transient immitivity response as a digital or analog output. A lack of a changing sensed voltage may indicate a lack of fluid between the electrodes. While this single time, or rate, measurement embodies the basis for the present invention, two or more measurements of the time-related response of this electrochemical cell system may be used to elucidate more subtle information.

The present invention is also a method of using an apparatus to obtain a transient immitivity response of a fluid. Initially, first and second electrodes are selected and the electrodes, spaced apart from each other, are brought into contact with a fluid. Time varying excitation voltage is then applied to the first electrode. The excitation voltage is subsequently switched between a first defined voltage level and a distinct second defined voltage level so that the first and second defined levels are alternately applied to the first electrode for specific time periods. The excitation source is further characterized by having a low resistance in order for a minimal switch time to exist when the excitation voltage is switched between the first and second defined voltage levels.

The method further includes providing a defined capacitance between the second electrode and an electrical or circuit ground. The ground has a defined voltage. A sense voltage is then detected as having been induced on the capacitance, the sense voltage being proportional to electrical charges conducted through the fluid from the first electrode to the second electrode as a consequence of the excitation voltage applied to the first electrode. The detector used is preferably characterized by having a high input resistance to minimize external current flows.

Following detection of a sense voltage induced on the capacitances, one or more time intervals are determined between the switch between first and second defined voltage levels and when the sense voltage at the second electrode attains one or more specific voltage levels. Alternately, one or more voltage levels attained at predetermined time intervals from the time the excitation voltage is switched between a first and second defined voltage level may be measured. These time intervals and voltage levels represent the transient immitivity response of the fluid and may be subsequently provided as digital or analog output.

It is known that the above-described resistances and capacitances are themselves functions of the fluid under test, fluid flow, temperature, electric potentials and other effects. The particular combinations of these effects as measured by the present invention can produce reduced dependence on flow and potential as well as reducing the variance in temperature dependencies caused by fluid composition.

It is therefore an object of the present invention to provide a fluid sensor which overcomes many of the limitations of the prior art.

It is another object of the present invention to provide a sensor for the presence of a variety of fluids and fluid bearing materials.

It is a further object of the present invention to provide a sensor which can qualitatively measure the difference between various solvents and fluid compositions.

Various other features, objects, and advantages of the invention will be made apparent to those skilled in the art from the accompanying drawings and detailed description thereof.

BRIEF DESCRIPTION OF THE SEVERAL VIEWS OF THE DRAWING

The previously stated features and advantages of the present invention will be apparent from the following detailed description as illustrated in the accompanying drawings wherein like reference numerals throughout the various figures denote like structural elements, and in which:

FIG. 1 is a schematic diagram showing the commonly accepted electronic analogue of a two-electrode electrochemical cell.

FIG. 2A is a graph showing a characteristic of a change in voltage.

FIG. 2B is a schematic diagram showing a capacitor.

FIG. 2C is a graph describing the reaction of the capacitor shown in FIG. 2B to the change in voltage shown in FIG. 2A, and the indirect currents induced by that change.

FIG. 3A is a graph showing a characteristic of a change in voltage the same as that shown in FIG. 2A.

FIG. 3B is a schematic diagram showing a capacitor and resistor connected in parallel.

FIG. 3C is a graph describing the reaction of the parallel resistance and capacitance (admittance) shown in FIG. 3B to the change in voltage shown in FIG. 3A.

DETAILED DESCRIPTION OF THE INVENTION

Figure 4A:
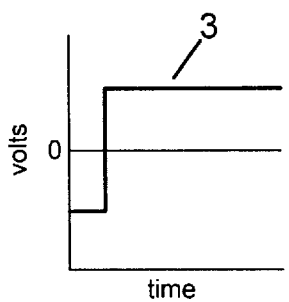
FIG. 4A is a graph showing a characteristic of a change in voltage the same as that shown in FIGS. 2A and 3A.

FIG. 1 is a schematic providing a known comparative view of electrochemical cell parameters and their electronic analogues relevant to the present invention. A two electrode electrochemical cell may be conceptually separated into a first or excitation electrode interface A, a fluid region B, and a second or sensing electrode interface C. FIG. 1 generally shows these three regions demarcated by vertical dashed lines. These three regions define a path for electrical current flow between the excitation electrode 1 and sensing electrode 2. The fluid region, B, has a known capacitance $C_f$ arising from atomic and molecular polarization as well as separation of any ionic species present in the fluid. The fluid also has a known conductivity, or electrical resistance $R_f$. Together, these two effects can be electrically modeled as a parallel resistance and capacitance, known as an admittance.

Still referring to FIG. 1, the two electrode interfaces, A and C, can also be electrically modeled as admittances. It is known that an electrode-fluid interface has a capacitance due to laminar molecular layers which form between the electrode and the diffuse bulk of the fluid. These are termed the Helmholtz layers, and establish a separation of charges, and thus a capacitance, $C_{ee}$ and $C_{se}$, similar to two very closely spaced plates of a capacitor. It is also known that the arrangement and capacitance of these layers is dependent on the electrical potentials present, which is not true of normal capacitors. Each electrode interface A and C also has known electrical resistance $R_{ee}$ and $R_{se}$ to current flow.

FIGS. 2A, 2B and 2C are a representation of the known electrical reaction of a capacitor C to a fast voltage change. FIG. 2A shows the electrical waveform 3 being impressed on one side of the capacitor C in FIG. 2B. The voltage on the excitation side of the capacitor C will rapidly follow the excitation voltage as long as sufficient current is available to charge the capacitor C in a short time. In this and the following examples, there is an assumed theoretical voltage source on the excitation side with an output impedance of zero, and an input amplifier on the sensing side that has high (>$10^{12}$ ohms) resistance and zero capacitance to ground. The excitation voltage starts at a low voltage and rapidly changes to a more positive voltage.

In FIGS. 2A–C, steady state, or direct current, voltage is blocked by the capacitor C. A rapid change in the excitation voltage, however, causes an indirect current. This is the result of the electrostatic fields within the capacitor C—when a charge is placed on one side, the charges on the other side reorganize to produce a charge equal to the excitation charge, but opposite in polarity. This results in a momentary, immediate current flow on the sensing side as the charges of the same polarity as the excitation voltage rush out and are replaced by charges of the opposite polarity. FIG. 2C shows the resultant voltage waveform 4 that would occur on the sense side of the capacitor C. The voltage measured is proportional to:

$$V_{out} = C * \frac{dV_{in}}{dt}$$

where: C=capacitance, t=time, $V_{in}$=change in excitation voltage.

As this equation shows, the pulse height is dependent on how quickly the excitation rat voltage ($V_{in}$) changes. Very fast rising voltages will produce a pulse height that is equal to the excitation voltage change, but never more. The amount of charge contained in a capacitor is related to the voltage present across it and its capacitance as:

$$q=CV$$

where: q=charge, C=capacitance, V=voltage across the capacitor.

The amount of current present in the resultant pulse on the sense side of the capacitor C is equal to the change in the charge of the capacitor C caused by the change in the excitation voltage. Since the present invention uses an input amplifier with a large, yet finite, input resistance, the charge will be drained through that resistance. If there were no path for current to flow from the sensing side, the voltage would remain equal to the excitation voltage as the capacitor C has reached an electrostatic equilibrium. If a lower resistance to ground is placed on the sense side, the pulse will shorten in width, as this charge is given a lower resistance path to ground and the charge is drained more quickly. For a very fast rising excitation voltage (time for excitation voltage change <Δt), this pulse shape will be equal to:

$$V_{out} = V_{in} * e^{\frac{-t}{RC}}$$

where: R=resistance to ground sensing side, C=capacitance, e=Euler's number (the base of a natural logarithm), and t=time increment.

This equation is the same as for discharging a capacitance, with good reason. The amount of charge 'stored' by a capacitor is the same as that absorbed from the excitation source and the same as that released in this indirect current. The capacitor does not actually store any net charge—it maintains a separation of charges. The current required to 'charge' the capacitor is actually transferred to its other side. In the process, a separation of charges is built up and maintained within the capacitor until the charges are allowed to recombine when the capacitor is discharged.

FIGS. 3A, 3B and 3C are a representation of an admittance and its reaction to a rapidly changing voltage. Once again, FIG. 3A shows the excitation waveform 3 consisting of a negative voltage that is rapidly switched to a positive voltage. The key difference in the circuit shown in FIG. 3B, from the circuit shown in FIG. 2B, is the inclusion of a parallel resistance $R_p$.

The indirect current passed through the parallel capacitor $C_p$ once again causes an immediate rise to the full excitation voltage. The current through the parallel resistance $R_p$ will maintain that voltage while also discharging the capacitor $C_p$, and the sensed waveform 5 will be as seen in FIG. 3C. If a lower resistance to ground is added to the sense side, the indirect current through the capacitor $C_p$ will still cause an immediate rise to the full excitation voltage change. The voltage will then drop at a rate determined by the resistance to ground, to a level that is determined by the voltage division of the parallel resistance $R_p$ and that resistance to ground.

Figure 4B:
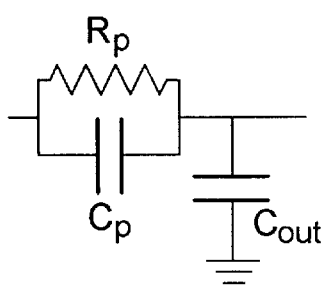
FIG. 4B is a schematic diagram showing an admittance with a capacitor connected between the output of the admittance and ground.

By comparison, FIG. 4B takes the admittance of FIG. 3B and adds a capacitance $C_{out}$ to ground on the sense side. As mentioned before, if a resistance is added to the output of the admittance, there will still be an immediate voltage rise from the indirect current through the capacitance $C_p$. Using a capacitance $C_{out}$ instead on the output provides a means for minimizing the voltage rise from the indirect current through the admittance capacitance $C_p$. That charge is immediately 'shared' between the two capacitances $C_p$ and $C_{out}$, reducing the immediate voltage rise sensed. The immediate voltage rise that will be seen is a result of the current division by the two capacitances $C_p$ and $C_{out}$ and is proportional to the ratio of the capacitances as:

$$V_{out} = V_{in} * \left(\frac{C_{out}}{C_p + C_{out}}\right)$$

While the output voltage is less than the input voltage, the two capacitors $C_p$ and $C_{out}$ will continue to draw current through the admittance resistance $R_p$ in order to charge the grounded capacitance $C_{out}$ and discharge the admittance capacitance $C_p$ to the input voltage level. These are complementary processes and are described by:

$$V_{out} = V_{in} * \left(1 - e^{\frac{-t}{R_p C_{out}}}\right) \qquad V_{out} = V_{in} * e^{\frac{-t}{R_p C_p}}$$

Ground capacitor charging    Admittance capacitor discharging

In practice, after the considerations for the initial, immediate, indirect current pass-through of the admittance capacitance $C_p$, the two capacitances $C_p$ and $C_{out}$ can be considered as two parallel charging capacitances. Parallel capacitances can be summed together in order to find their combined influence, thus:

$$V_{out} = V_{in} * \left(1 - e^{\frac{-t}{R_p(C_p + C_{out})}}\right)$$

Combining the above equation with that for the current sharing of the indirect current through the admittance capacitor $C_p$, and putting it in terms of the grounded capacitor $C_{out}$ we get:

$$V_{out} = V_{in} * \left[1 - \left(\frac{C_{out}}{C_p + C_{out}}\right) * e^{\left(\frac{-t}{R_p(C_p + C_{out})}\right)}\right]$$

Figure 4C:
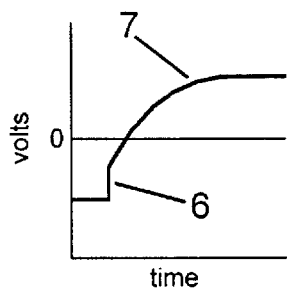
FIG. 4C is a graph that shows the reaction of the admittance to the voltage change of FIG. 4A when the capacitance is placed between the sensing end and electrical ground.

This equation gives an accurate description of the output voltage from the circuit represented in FIGS. 4A–C in the special case of a rapid and discrete change in $V_{in}$ (time for excitation voltage change <Δt) from 0 Volts to $V_{in}$. The output waveform shown in FIG. 4C shows the immediate voltage rise 6 and the charging/discharging waveform 7 described by the equation above, but adjusted for a bipolar excitation source voltage.

One notable feature of this circuit is that the effect of the capacitance of $C_p$ is more prominent in the term for the indirect current than for the charging current. In other words, $C_p$ affects the output voltage rise time more by shortening it through the indirect current passed through than by the lengthening of the rise time through discharging through the parallel resistance $R_p$. The reason is that the indirect current is passed through immediately where the charge/discharge current is time-related. This reverses the expected effect of the admittance capacitance of $C_p$—a larger value actually shortens the overall rise time of the circuit, governed by:

$$V_{in} - V_{in} * \frac{C_{out}}{C_p + C_{out}}$$

The admittance circuit shown in FIGS. 3B and 4B can also be used as a simplification of the general electrochemical schematic shown in FIG. 1. In this case, the circuit of FIG. 1 is regarded as an admittance of the series combination of resistances $R_{ee}$, $R_f$ and $R_{se}$ in parallel with the series combination of capacitances $C_{ee}$, $C_f$ and $C_{se}$. In other words, the admittance values of FIGS. 3B and 4B would be replaced by:

$$R_p = R_{ee} + R_f + R_{se}$$

and:

$$C_p = \frac{1}{\frac{1}{C_{ee}} + \frac{1}{C_f} + \frac{1}{C_{se}}}$$

When used in the equations above, this gives a good first approximation and simplified description of the actions of this circuit. A further interesting point can be seen from the equations above—that the smaller capacitance of the three admittance capacitors will have the greatest effect on the circuit. This is important because the fluid capacitance $C_f$ will almost always be much smaller than the capacitance of the electrode interfaces $C_{ee}$ and $C_{se}$. This stems quite simply from the geometry of the probe used, where the capacitance can be calculated from the general equation for a simple flat plate capacitor:

$$C = \frac{\varepsilon A}{D}$$

where: $\varepsilon$=overall permitivity, A=area of each plate, and D=distance between plates.

From the above, the greater the distance between the plates, the smaller the capacitance. At the electrode interfaces A and C of FIG. 1, the distances between the 'plates' of the capacitance's $C_{ee}$ and $C_{se}$ are on a molecular level, the distance from the electrode surface to that of the 'diffuse' layer and/or the Helmholtz layers, and measured in Angstroms or nanometers. The electrodes themselves will normally be separated by a range from micrometers to decimeters, the distance for the fluid capacitance $C_f$. In this process the fluid capacitance $C_f$ dominates, which helps to eliminate some of the electrochemical effects that affect the capacitances $C_{ee}$ and $C_{se}$ of the electrode interfaces A and B, such as their known variation with applied voltage.

If there is little or no path to ground on the sensing side, i.e. when the sensing amplifier impedance is very high, the only currents that pass through the admittance are those required to discharge the admittance capacitance $C_p$ and charge the output capacitance $C_{out}$. This limits the amount of current drawn through the fluid thereby reducing the possibilities of chemical changes on the surfaces of the electrodes and in the fluid. These effects can be further reduced by using a bipolar excitation voltage and/or having the excitation voltage connected only when a measurement is made.

Also, when using a high input resistance input amplifier, the sensed voltage will be near or equal to the input voltage when the cell is at equilibrium, so the sensed voltage will be as large as that input. This means that little or no signal conditioning or amplification will be needed. Adding a smaller resistance to ground at the input amplifier will decrease the sensed voltage and cause additional currents to constantly flow through the cell.

The present invention measures the time it takes for the sensed voltage to reach a particular voltage or the voltage reached at a particular time. While any voltage level could be used for the former, using a level that is 0 volts for a bipolar excitation, or half the excitation voltage for an excitation that runs to and from ground, can make the design simpler and help reduce the effects of electrical noise. This time interval, or voltage, gives a single measurement of the complex effects described herein. Such measurements are well known and well suited for digital circuitry or conversion to analog signals.

Most fluids have a predictable reaction to increased temperatures, both the fluid resistance and capacitance decreasing at differing, and often non-linear, rates. Other methods can require complex compensations to account for these changes, particularly when the fluid composition is subject to change. In the present invention, the various design elements, probe configuration and input capacitance, can be adjusted so that the system 'self-compensates' for many of the temperature changes. If the capacitance of the fluid goes down with increased temperature, it can increase the transient immitivity response, whereas a decrease of fluid resistance will work to decrease the transient immitivity response.

Figure 5:
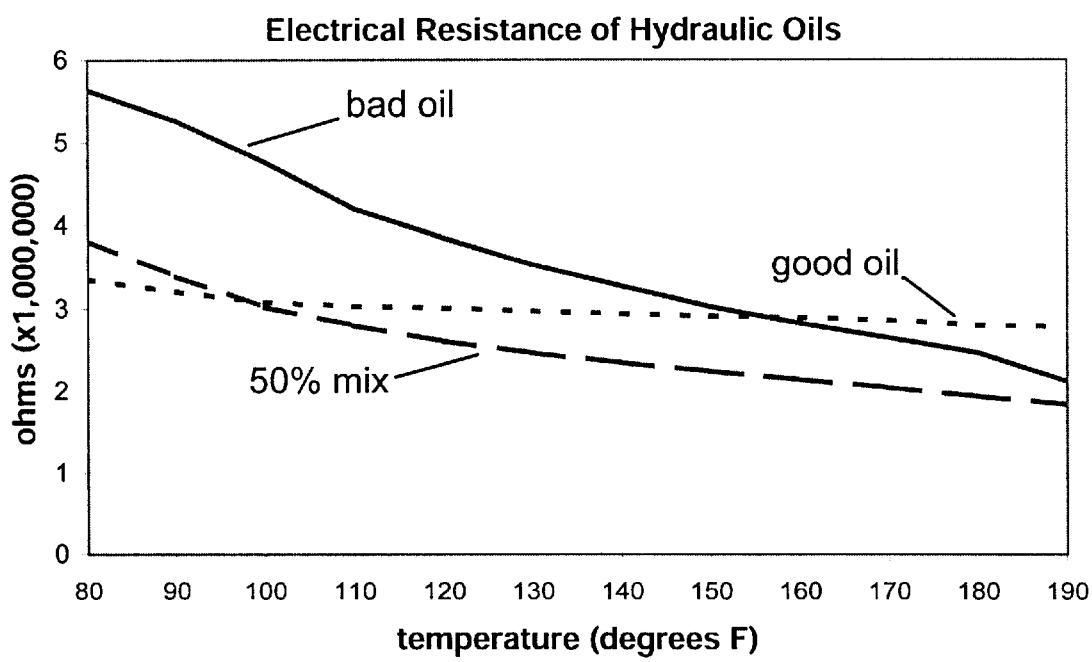
FIG. 5 is a graph showing the result of a study of the electrical resistance of certain aircraft hydraulic oils over a range of temperatures.
Figure 6:
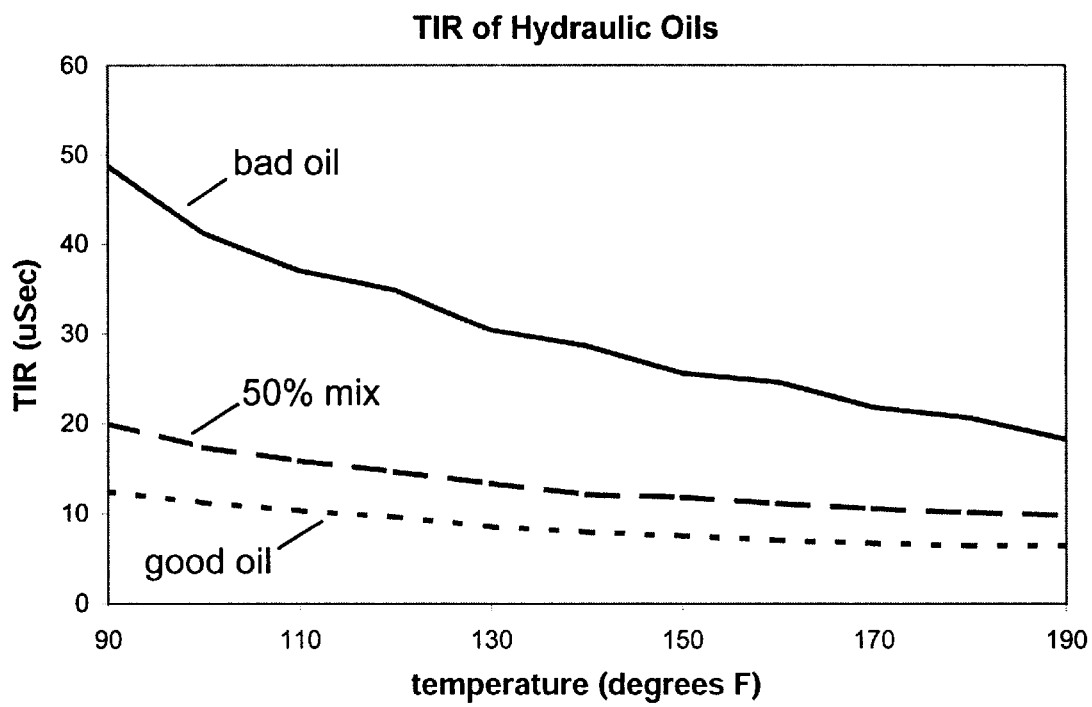
FIG. 6 is a graph showing the results of measurements of certain aircraft hydraulic oils over a range of temperatures according to a preferred embodiment of the present invention.

FIGS. 5 and 6 represent data from a study on aircraft hydraulic oils. For cost reasons, these oils are never completely replaced in the aircraft systems. Instead, the guidelines given airline maintenance crews are to top off any loss of oil. The particular breakdown pattern of this oil creates an acidic content that can cause destructive corrosion of hydraulic system parts. The two graphs shown in FIGS. 5 and 6 represent readings of fluid resistance and the present invention measurements made on a sample of new oil, well used oil, and a 50:50 mixture of the two, respectively.

Specifically, FIG. 5 is a set of resistance readings taken on the above-described samples over a variety of temperatures and shows the problems that can be encountered in using resistance (or conductance) measurements over a range of temperatures. In both examples, the same simple two copper wire probe was used. For resistance, a Hewlett Packard (HP) 5300 measuring system with an HP 5306A multimeter was used. In use, temperature compensation for this method would be impossible, as the readings for the new oil cross over those of the other samples. Even if one knew the particular temperature a reading was taken at, the compensation could not be known as it would be impossible to separate the composition effects from the temperature effects.

FIG. 6 shows the results using the present invention. For measurements using the present invention, a GW GFG8016G function generator was used as the excitation source and a Tektronix TDS 210 oscilloscope was used for measurements, with a x10, 10 Mohm probe. The capacitance of this probe and the input circuitry of the oscilloscope itself was used as the input capacitor, $C_{out}$. FIG. 6 shows that the composition and temperature effects can be clearly separated using this process. In this case, a simple temperature compensation would be required to allow accurate qualitative measurement of the oil over a wide temperature range.

Figure 7:
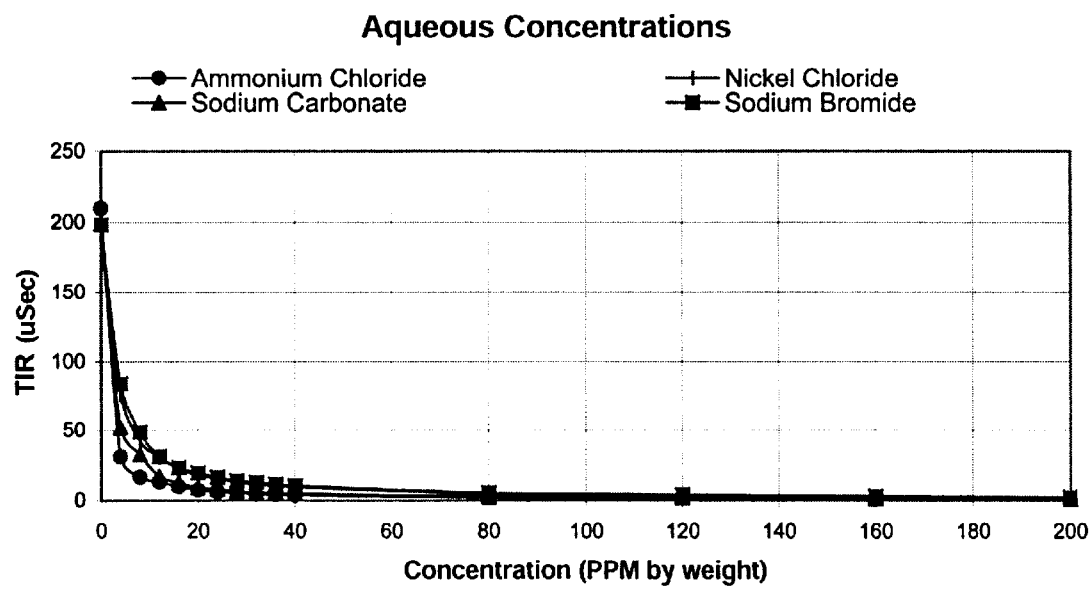
FIG. 7 is a graph of the measurements of a number of aqueous solutions over a range of concentrations, using a preferred embodiment of the present invention.

FIG. 7 shows the result of concentration measurements using the present invention on four different aqueous solutions. These results show that this process produces ionic sensitivity similar to typical conductivity measurements. In this case, these compositions make little change to the dielectric constant of the water but do change the fluid resistance which affects the charge/discharge of $C_{out}$ and $C_p$. Measurements in the PPB range or less are clearly possible, with the sensitivity greatest for smaller concentrations.

More importantly, FIG. 6 and FIG. 7 show the wide range of fluids that can tested using the present invention. By adjusting the probe design and sensing amplifier input capacitance, virtually any fluid or fluid bearing material can be qualitatively tested using this process.

Figure 8A:
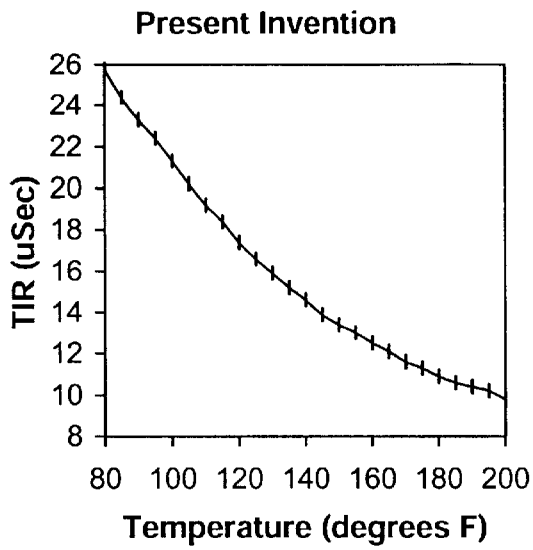
FIGS. 8A–D are graphs showing the results of a comparison study of the temperature characteristics of various known methods and the present invention on distilled water.
Figure 8B:
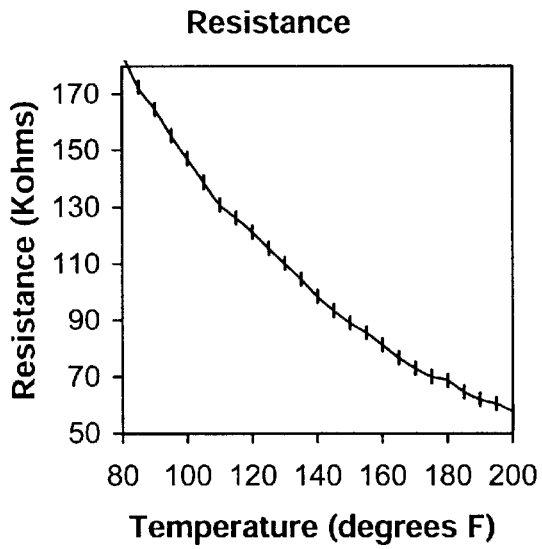
Figure 8C:
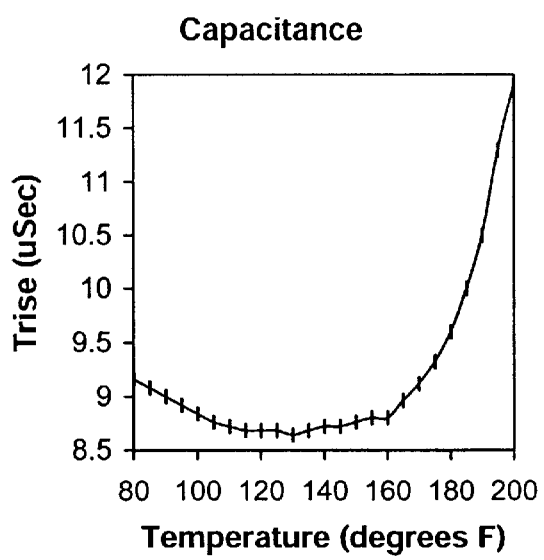
Figure 8D:
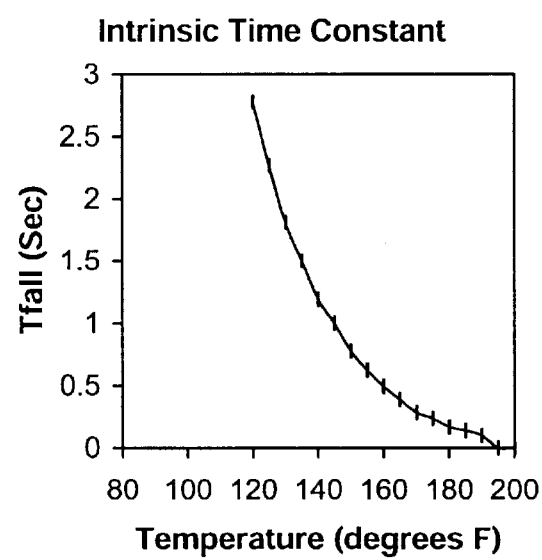
Figure 9A:
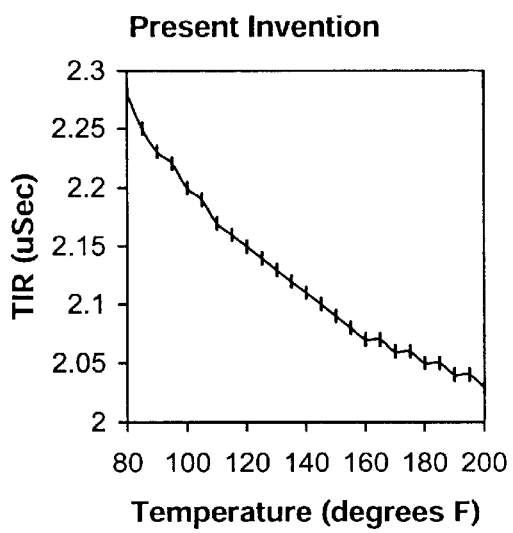
FIGS. 9A–D are graphs showing the results of a comparison study of the temperature characteristics of various known methods and the present invention on tap water.
Figure 9B:
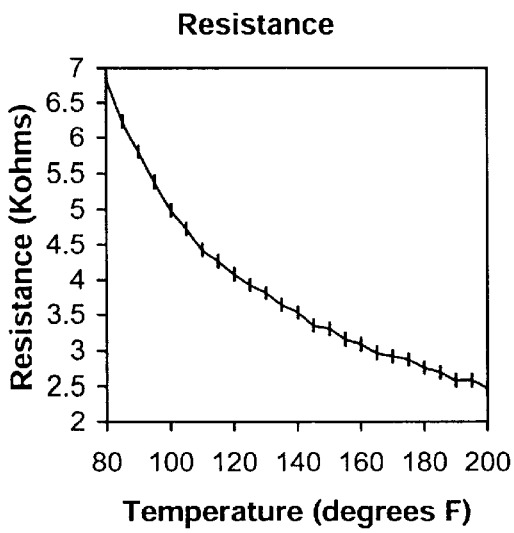
Figure 9C:
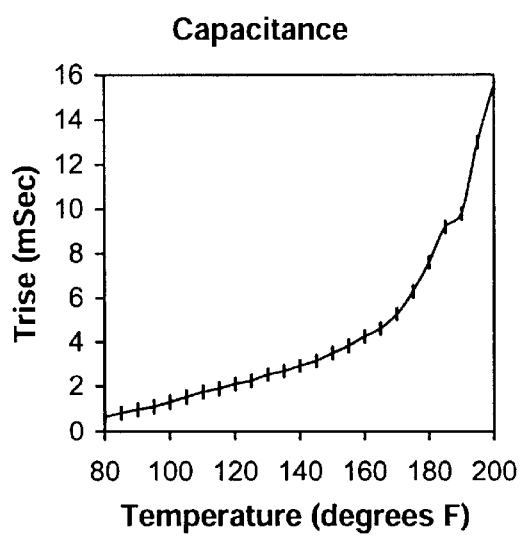
Figure 9D:
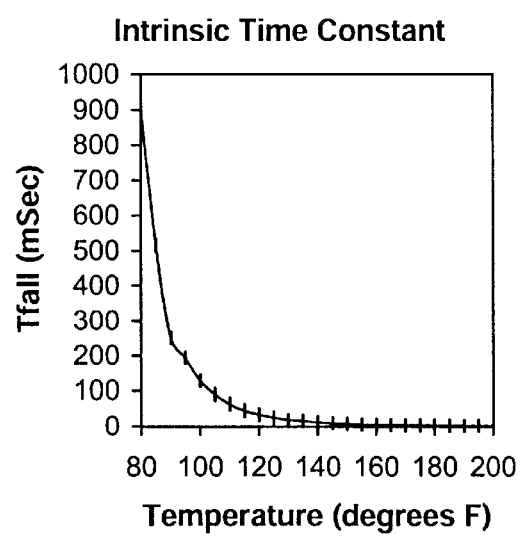

FIGS. 8A–D, 9A–D and 10A–D show comparisons of the present invention, assembled as described for FIG. 6, and three common methods: conductivity, capacitance and intrinsic time constant. FIGS. 8A–D show the results using the present invention in FIG. 8A, and the other three methods, FIG. 8B, showing resistance, or the reciprocal of conductivity, FIG. 8C, showing capacitance, and 8D, graphing the intrinsic time constant, all on distilled water over a range of temperatures from 80 to 200 degrees Fahrenheit. FIGS. 9A–D show the results of using the four methods, respectively, on tap water over the same temperature range. FIGS. 10A–D respectively compare the results for each method, with the result using distilled water being graphed against that for tap water.

Tap water was chosen as a common, complex electrolyte. In comparing the results shown in FIGS. 8A–D and FIGS. 9A–D, it is clear that each method, excluding that of the present invention, has a response to temperature variations that depends in varying degree to the fluid composition, and thus a different characteristic curve for each. In FIGS. 8A–D and 9A–D the present invention has a characteristic temperature response that is very similar.

Figure 10A:
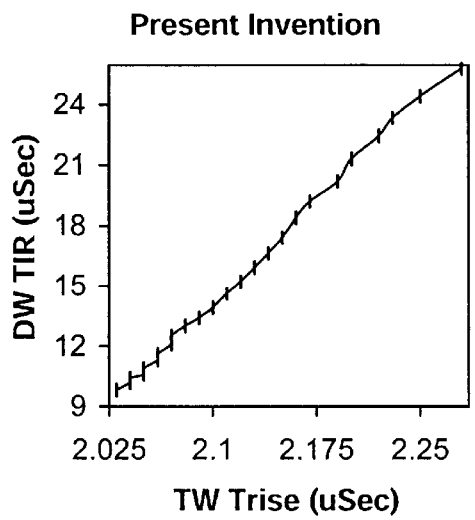
FIGS. 10A–D are graphs showing the results in FIGS. 8A–D and FIGS. 9A–D, respectively, in a manner representing the temperature characteristics of these methods in relation to compositional changes.
Figure 10B:
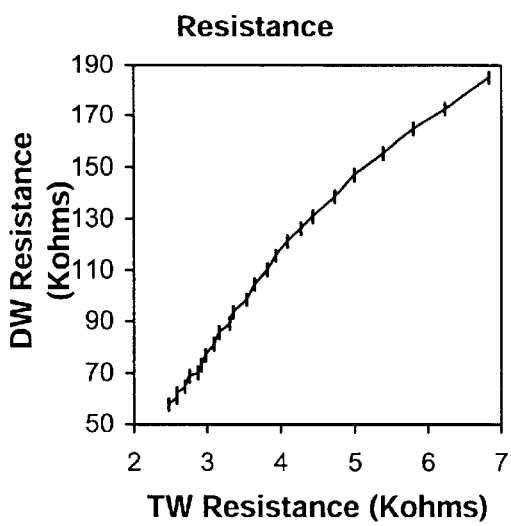
Figure 10C:
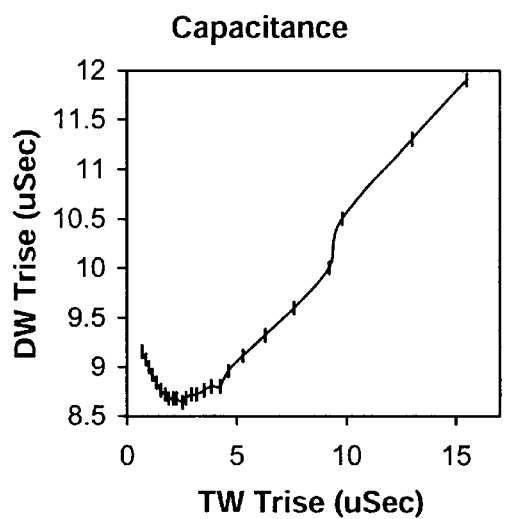
Figure 10D:
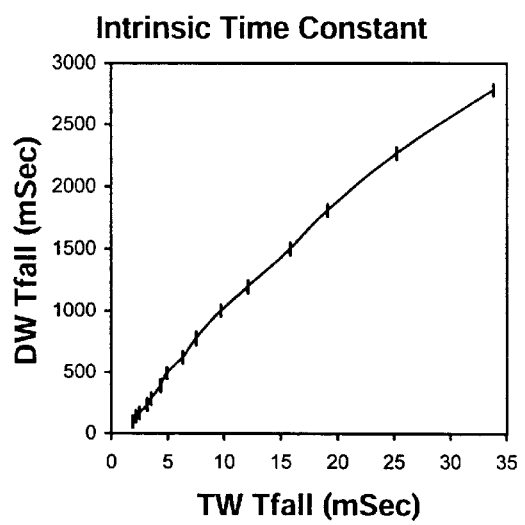

In FIGS. 10A–D, these differences are further brought out by graphing the response to distilled water against that for tap water for each method. FIG. 10A, representing the present invention, shows a very linear relationship between its temperature response for distilled water and tap water. This means that, while the measurements clearly show a sensitivity to the composition of these fluids, the present invention has an insensitivity to temperature related effects caused by compositional changes. FIGS. 10B, 10C and 10D show that these three known methods have temperature responses that vary considerably according to fluid composition.

For accurate use of any qualitative fluid sensing system, temperature compensation is required. These graphs show that the three known methods, conductivity, capacitance and intrinsic time constant, would also require some knowledge of the fluid composition in order to effect an accurate temperature compensation. However, for the present invention, a single compensation, requiring knowledge of the temperature alone, would be useable over a wide range of temperatures and fluid compositions.

Figure 11A:
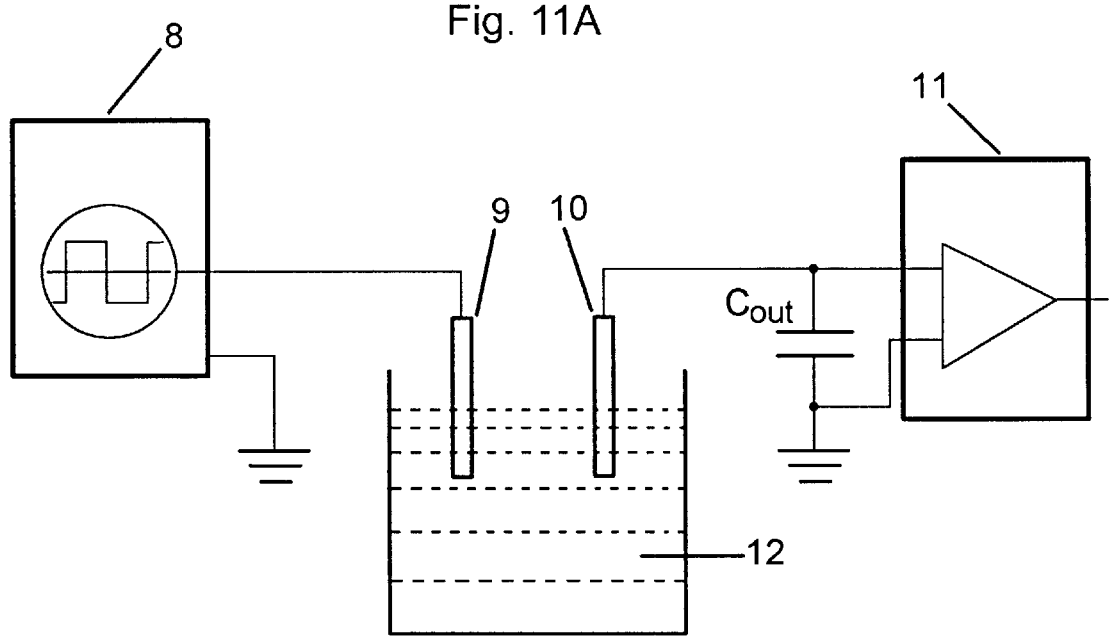
FIG. 11A is a schematic diagram depicting a measurement arrangement according to one embodiment of the present invention.
Figure 11B:
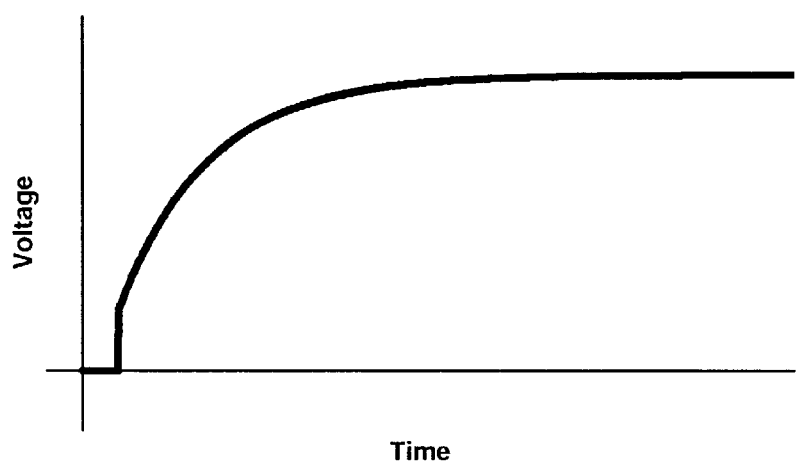
FIG. 11B is a representative waveform measured by the arrangement of FIG. 11A.

FIG. 11A shows a basic measurement setup according to the present invention. An excitation signal source 8 is connected directly to excitation electrode 9. Electrodes 9 and 10 are submersed in sample fluid 12. Sense electrode 10 is connected to input amplifier 11 with $C_{out}$ as the input capacitance. Any particular single measurement using the present invention gives a value that is a representation of the various electrochemical effects in the cell, primarily the resistances and capacitances of the fluid and electrode interfaces. FIG. 11B shows a representative waveform that would be measured by this circuit.

Figure 12A:
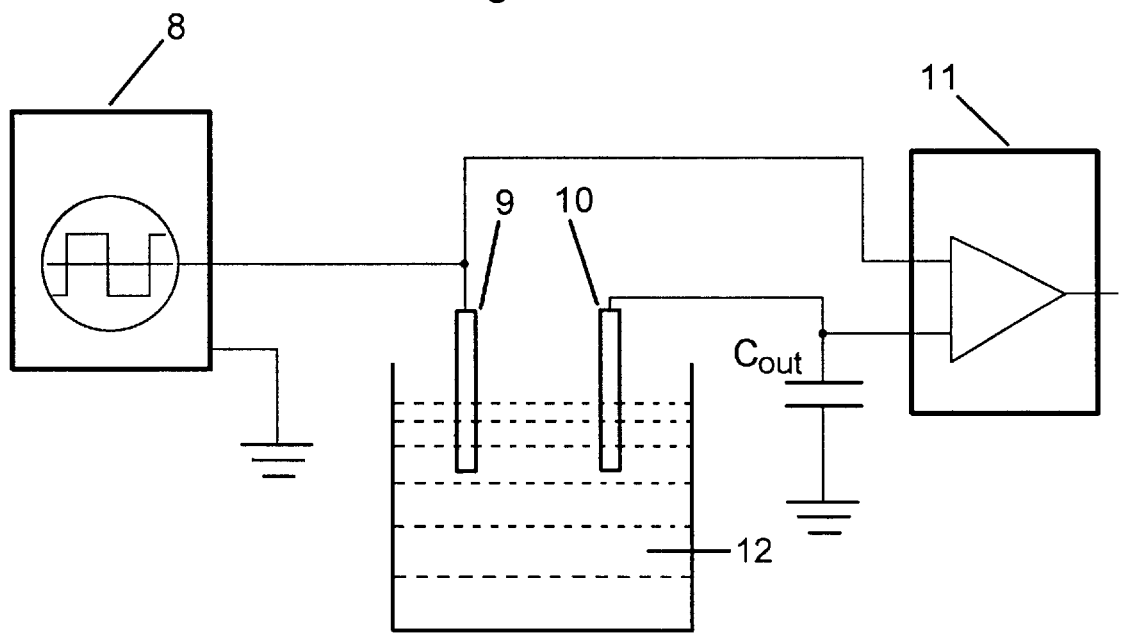
FIG. 12A is a schematic diagram depicting a measurement arrangement according to an alternative embodiment of the present invention.
Figure 12B:
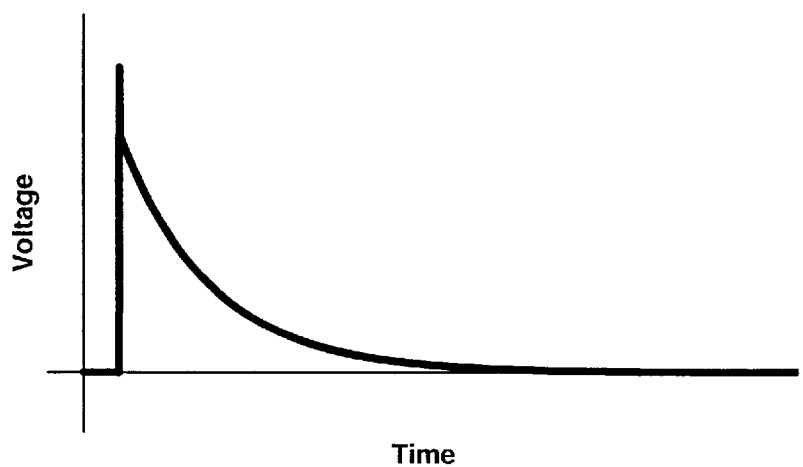
FIG. 12B is a representative waveform measured by the arrangement of FIG. 12A.

FIG. 12A shows an alternate embodiment according to the present invention. In this embodiment, a differential amplifier (11) is used to measure the voltage difference between the excitation (9) and sensing (10) electrodes. Subtracting the voltage on the sensing electrode (10) from that on the excitation electrode (9) gives a measure of the state of equilibrium of the cell. When at equilibrium, there will be a voltage close to zero as both electrodes are at virtually the same voltage. When the excitation voltage is switched to a new voltage level, this output voltage will immediately rise to the difference in voltage states and decay back to near zero volts as the if cell comes to equilibrium to the new excitation voltage, as shown in FIG. 12B. This pulse output may also be measured for the time interval to a specific voltage level or the voltage at a specific time interval, either one, again, a measurement of the transient immitivity response.

Figure 13A:
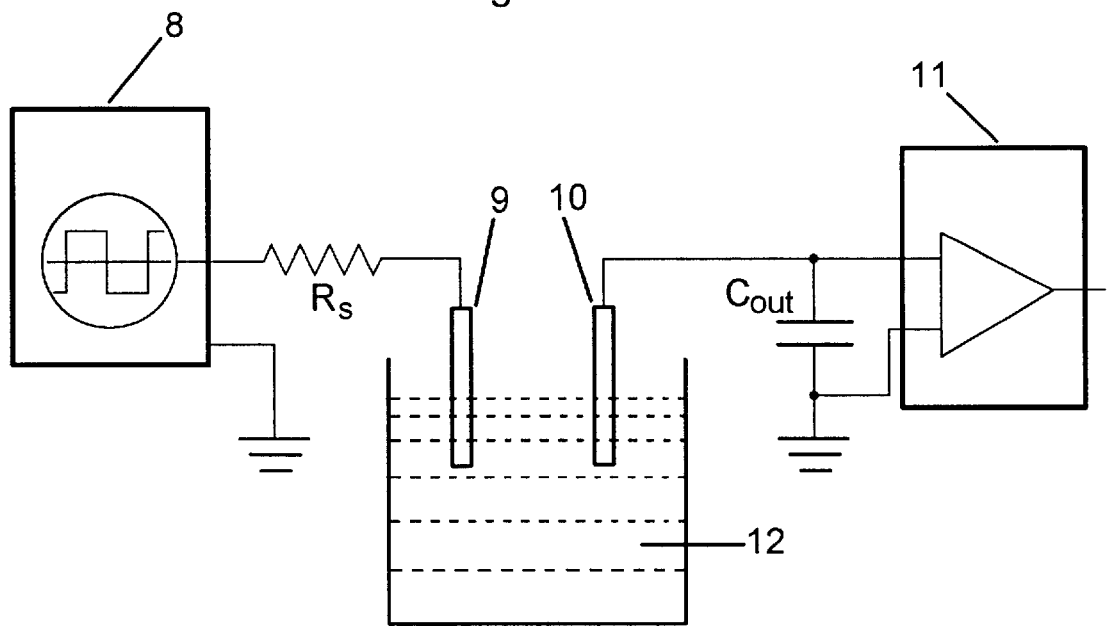
FIG. 13A is a schematic diagram depicting a measurement arrangement according to another alternative embodiment of the present invention.
Figure 13B:
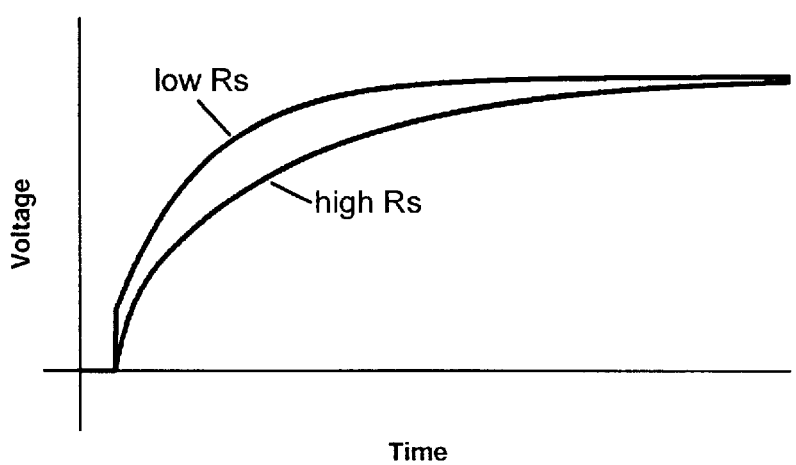
FIG. 13B shows representative waveforms measured by the arrangement of FIG. 13A.

FIG. 13A shows another alternative embodiment according to the present invention, including the addition of a series resistance $R_s$. In this embodiment excitation signal source 8 is connected through series resistance $R_s$ to excitation electrode 9. Electrodes 9 and 10 are submersed in sample fluid 12. Sense electrode 10 is connected to input amplifier 11 with $C_{out}$ as the input capacitance. By taking two or more measurements, each with a different value for series resistance $R_s$ (one can be zero resistance), the difference between the two measurements is primarily the result of the time constant formed between the series resistance $R_s$ and the capacitances of the system. FIG. 13B shows two representative waveforms generated by this embodiment, one from a low $R_s$ and one from a high $R_s$.

Figure 14:
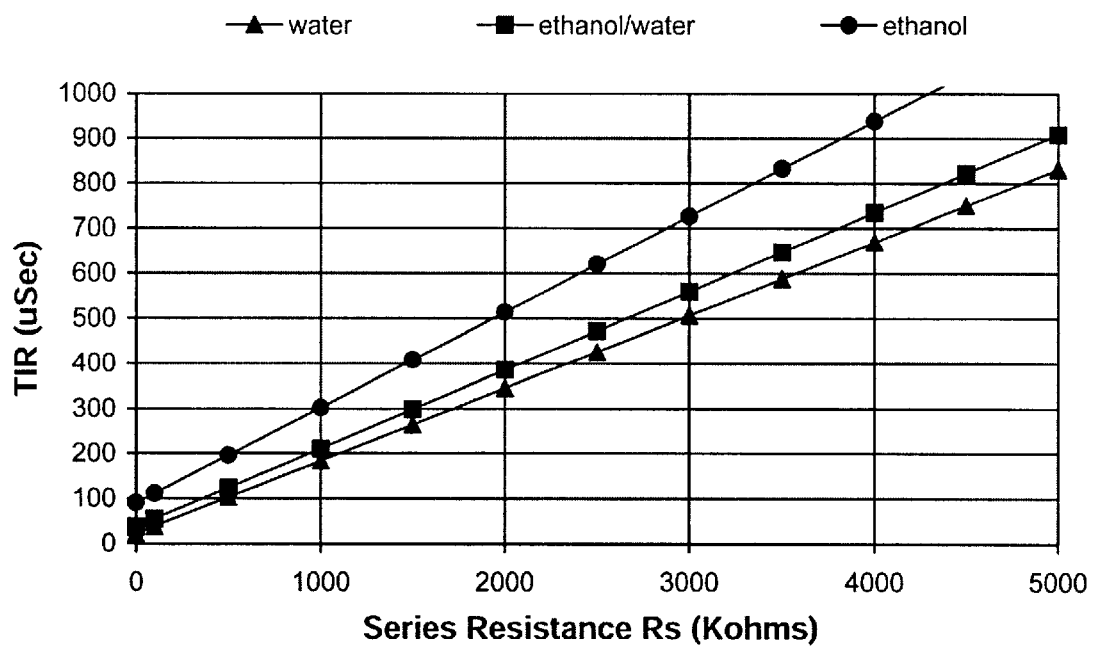
FIG. 14 is a graph showing the results of using the embodiment shown in FIG. 13A to determine the electrical capacitances of a cell.

FIG. 14 shows how using the measurements described in the preceding paragraph and shown in FIG. 13B can differentiate between qualitative changes due to solvent changes. In FIG. 14, samples of distilled water, ethanol, and a 50% mixture of the two, have their rise times plotted against the series resistance $R_s$. Each has a clearly distinguishable slope. Essentially, the slope is proportional to the capacitances and thus the fluid's dielectric constant.

Figure 15:
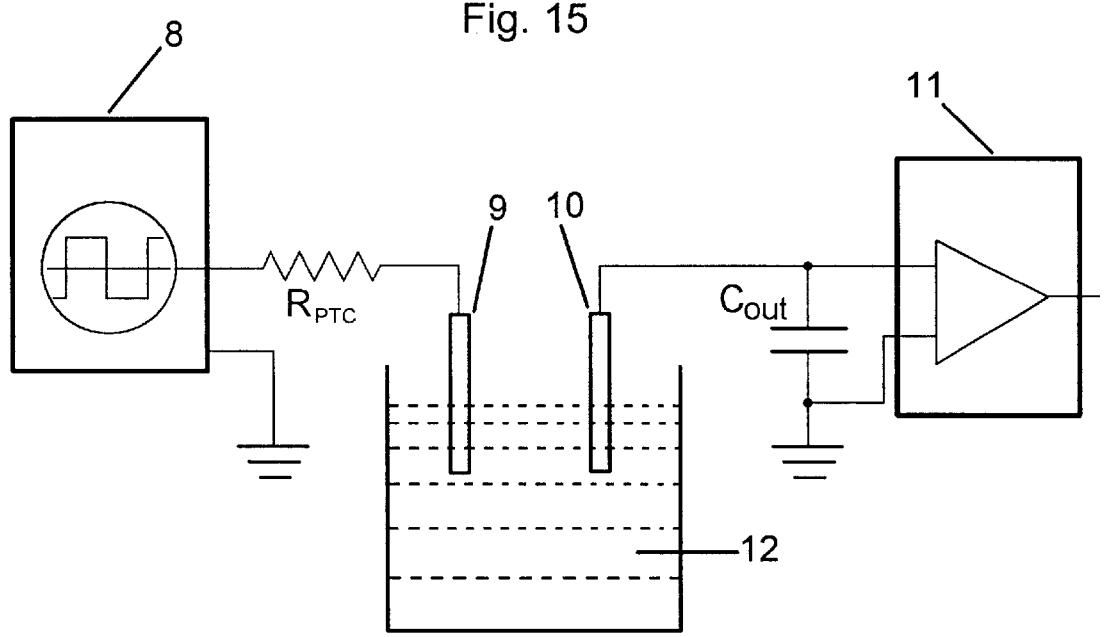
FIG. 15 is a schematic diagram depicting a measurement arrangement according to yet another alternative embodiment of the present invention.

FIG. 15 shows yet another embodiment of the invention similar to the circuit shown in FIG. 13 which included the addition of a series resistance. In FIG. 15, the use of an electronic component the resistance of which changes with temperature can effect a simple temperature compensation means. By placing such an element $R_{PTC}$, such as a thermistor, a resistance network including one or more thermistors, or a circuit capable of changing the resistance $R_s$ in response to temperature changes, in place of the series resistance, $R_s$, and placing element $R_{PTC}$ in thermal contact with the fluid, a self-compensating probe may be constructed. Properly matched to the probe and fluid, element $R_{PTC}$ can change the transient immitivity response as the temperature changes in order to compensate for the change in temperature. As previously shown, the present invention can be very insensitive to compositional temperature dependencies, making a self-compensated probe as described useable over a wide range of temperatures and fluid compensations.

Figure 16A:
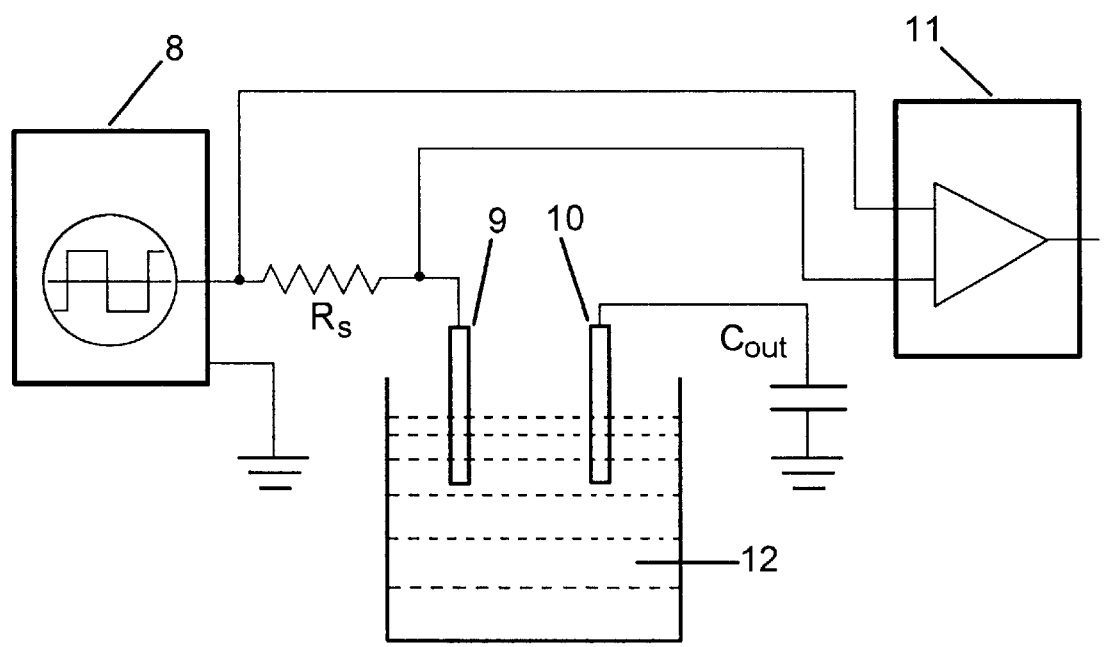
FIG. 16A is a schematic diagram depicting a measurement arrangement according to another alternative embodiment of the present invention.
Figure 16B:
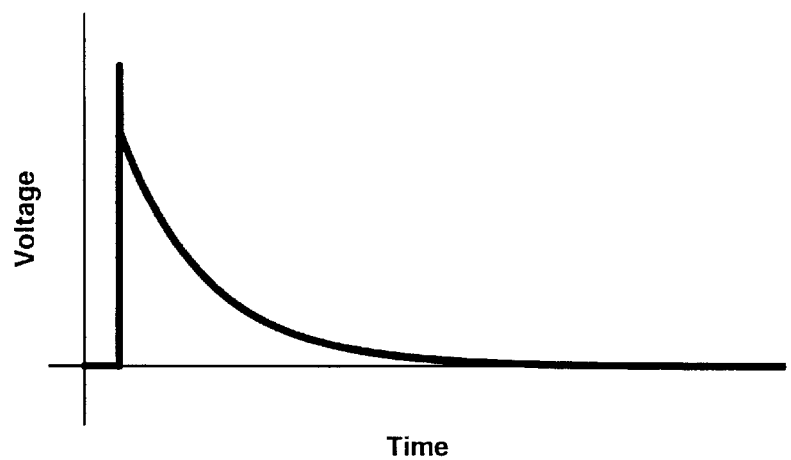
FIG. 16B is a representative waveform measured by the arrangement of FIG. 16A.

FIG. 16A, another embodiment of the invention, shows the addition of a series resistance on the excitation source. This embodiment allows the measurement of the current going into the cell, as opposed to the current that has passed through the cell to the input capacitance. In this embodiment, the voltage sensing means is connected across the series resistance, $R_s$. The voltage measured will be the current being drawn by the cell multiplied by the resistance of $R_s$, and the output waveform is represented in FIG. 16B. In this case, the ultimate height of the voltage waveform can change along with the transient immitivity response as the maximum amount of current drawn will be primarily determined by the series resistance, $R_s$, and the excitation electrode interface capacitance, $C_{ee}$. This peak voltage change can be used to increase the sensitivity of the measurement under some conditions as well as provide a measurement primarily of the excitation electrode capacitance, $C_{ee}$.

Figure 17A:
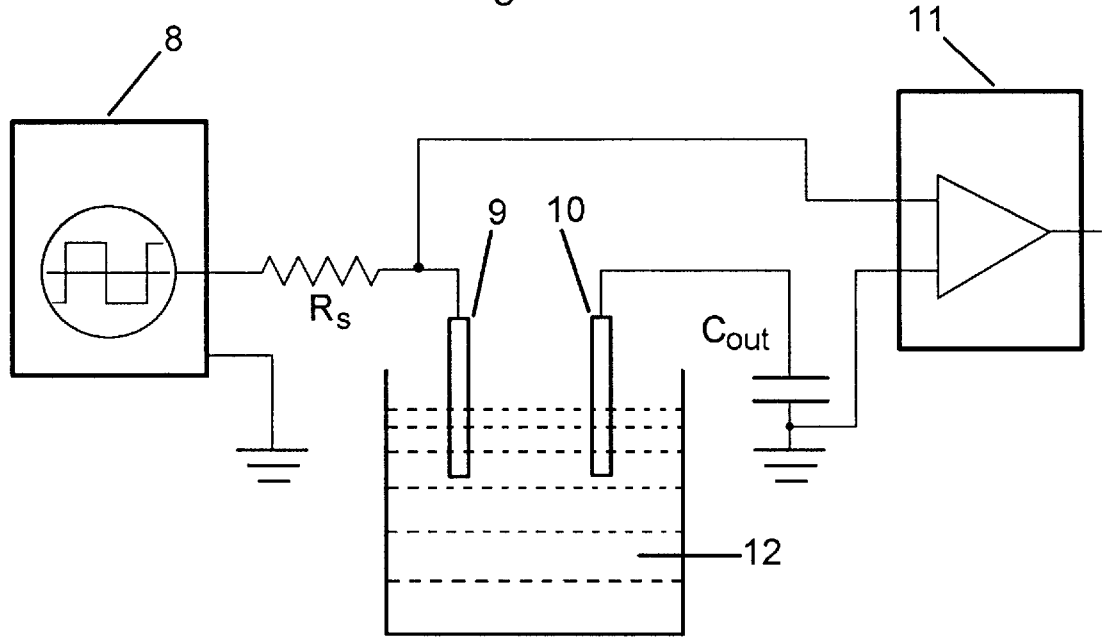
FIG. 17A is a schematic diagram depicting a measurement arrangement according to still another alternative embodiment of the present invention.

FIG. 17A shows yet another alternate embodiment somewhat similar to that shown in FIG. 16. In this embodiment, the voltage detection means is connected to the excitation electrode and circuit ground. The voltage detection means is connected to the excitation electrode and circuit ground. The voltage measured will be the result of the excitation voltage minus the voltage across $R_s$ caused by the current through $R_s$ as:

$$V_{out} = V_{in} - (I_{R_s} * R_s)$$

Figure 17B:
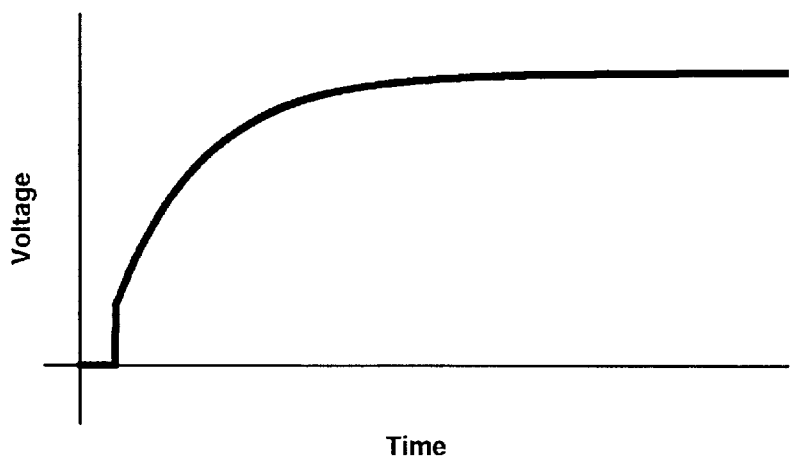
FIG. 17B is a representative waveform measured by the arrangement of FIG. 17A.

FIG. 17B shows the waveform resulting from the circuit of FIG. 17A. In this case, the ultimate voltage achieved will essentially be $V_{in}$, rather than a voltage determined by the current drawn through $R_s$ as in the circuit of FIG. 16A.

Figure 18A:
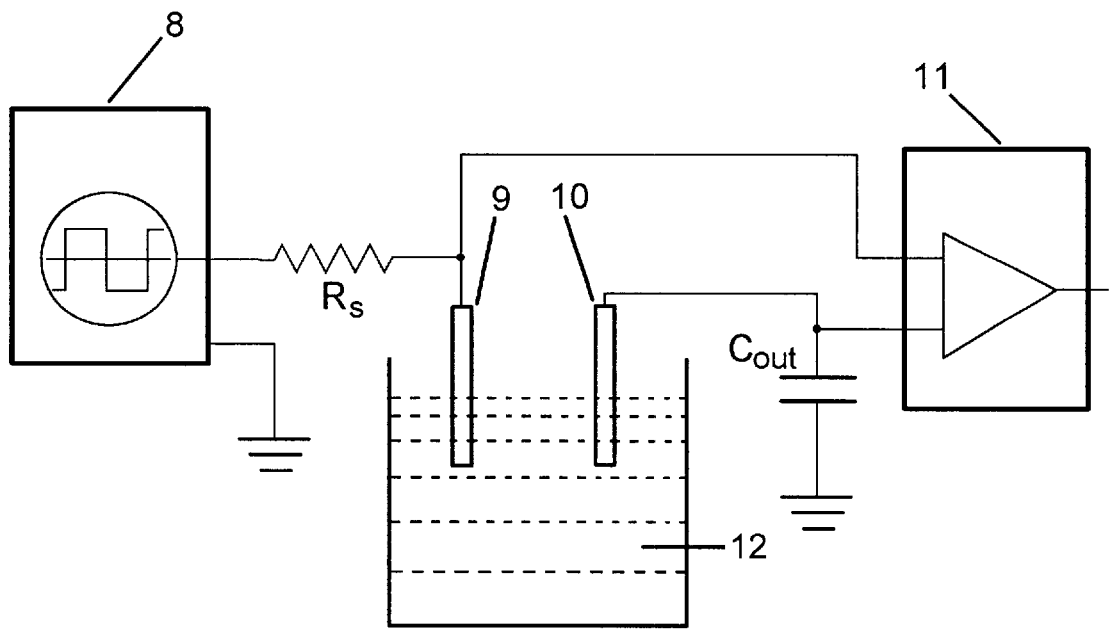
FIG. 18A is a schematic diagram depicting a measurement arrangement according to another alternative embodiment of the present invention.
Figure 18B:
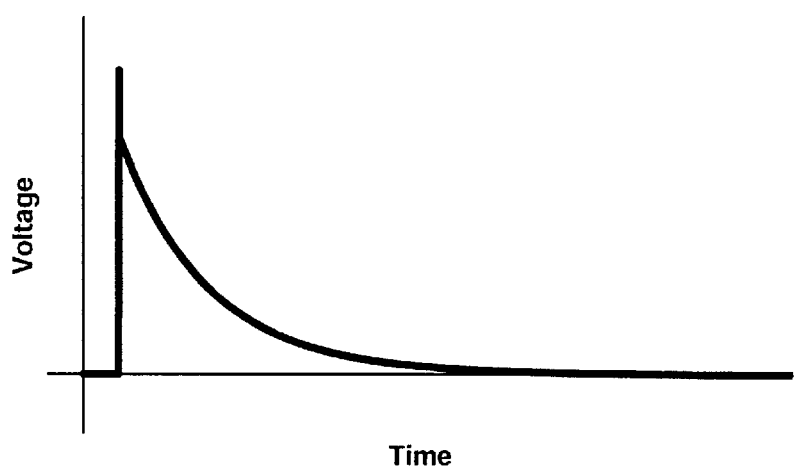
FIG. 18B is a representative waveform measured by the arrangement of FIG. 18A.

FIG. 18A shows another embodiment of the invention, wherein the voltage sensing means is connected to the excitation electrode 9 and the sensing electrode 10, as in FIG. 12A. In this embodiment, though, similar to FIGS. 13 through 17, the series resistance $R_s$ is used between the excitation source 8 and the excitation electrode 9. FIG. 18B shows a representative waveform from this embodiment. As in FIGS. 12A–B, this embodiment produces a voltage pulse that represents the state of equilibrium of the cell, but the ultimate voltage height of this pulse will be limited to the excitation voltage input minus the voltage drop across the series resistance $R_s$, as a result of the current drawn through it.

While the invention has been described with reference to preferred embodiments, those skilled in the art will appreciate that certain substitutions, alterations, and omissions may be made without departing from the spirit of the invention. Accordingly, the foregoing description is meant to be exemplary only and should not limit the scope of the invention set forth in the following claims.

What is claimed is:

1. An apparatus for obtaining a transient immitivity response for a fluid, comprising:
    a first electrode and a second electrode, the first and second electrodes being spaced apart from each other and both in contact with the fluid;
    an excitation source for providing a time varying excitation voltage to the first electrode, the excitation voltage being capable of being switched between a first defined voltage level and a distinct second defined voltage level;
    a capacitance located between the second electrode and an electrical or circuit ground, the ground having a defined ground voltage;
    a voltage detector for detecting a sensed voltage at a predetermined location with respect to the apparatus; and
    a timing device for determining one or more time intervals between the switch in first and second defined voltage levels wherein the one or more time intervals can be correlated with the sensed voltage at each interval and each sensed voltage per time interval measures a rate representing the transient immitivity response.

2. An apparatus as recited in claim 1, wherein the first and second voltage levels are alternately applied to the first electrode for specific time periods.

3. An apparatus as recited in claim 1 wherein the sensed voltage is proportional to electrical charges conducted through the fluid from the first electrode to the second electrode as a consequence of the excitation voltage applied to the first electrode.

4. An apparatus as recited in claim 1 wherein the voltage detector has a high input resistance to minimize external current flows.

5. An apparatus as recited in claim 1 wherein the timing device is capable of determining when the sensed voltage attains one or more selected voltage levels.

6. An apparatus as recited in claim 1 wherein the voltage detector is capable of determining the sensed voltage at one or more time intervals.

7. An apparatus as recited in claim 1 wherein the rate established by the sensed voltage change per time interval representing the transient immitivity response of the fluid is provided as a digital or analog output.

8. An apparatus as recited in claim 1 where the excitation source has a minimal output resistance such that the capacitance of the first electrode is charged instantaneously upon receiving the excitation voltage.

9. An apparatus as recited in claim 1 wherein the voltage detector is connected to measure voltage across the capacitance.

10. An apparatus as recited in claim 1 wherein the voltage detector is connected to measure voltage between the first electrode and the second electrode.

11. An apparatus as recited in claim 1 wherein a series resistance is electrically connected between the excitation source and the first electrode.

12. An apparatus according to claim 11 wherein the voltage detector is connected to measure voltage across the capacitance.

13. An apparatus according to claim 11 wherein the voltage detector is connected to measure voltage across the series resistance.

14. An apparatus according to claim 11 wherein the voltage detector is connected to measure voltage between the ground and the first electrode.

15. An apparatus according to claim 11 wherein the voltage detector is connected to measure voltage between the first and second electrodes.

16. An apparatus according to claim 1 wherein a variable resistance responsive to changes in temperature of the fluid is connected between the excitation source and the first electrode.

17. An apparatus for obtaining a transient immitivity response for a fluid, comprising:
    a first electrode and a second electrode, the first and second electrodes being spaced apart from each other and both in contact with the fluid;
    an excitation source providing a time varying excitation voltage to the first electrode, the excitation voltage being switched between a first defined voltage level and a distinct second defined voltage level, the first and second voltage levels being alternately applied to the first electrode for specific time periods;
    a capacitance located between the second electrode and an electrical or circuit ground, the ground having a defined ground voltage;
    a detecting means capable of detecting an electrical charge conducted through the fluid as a consequence of the excitation voltage applied to the first electrode, wherein the detecting means has a high input resistance to minimize external current flows; and
    a determining means capable of determining one or more rates of change in the electrical charge per time interval, such one or more rates representing the transient immitivity response of the fluid, the determining means capable of providing the transient immitivity response as a digital or analog output.

18. A method for obtaining a transient immitivity response, comprising the steps of:
   a) contacting a fluid with a first electrode and a second electrode, the first and second electrodes spaced apart from each other;
   b) applying an excitation voltage to the first electrode and switching the excitation voltage between a first defined voltage level and a distinct second defined voltage level;
   c) providing a capacitance between the second electrode and an electrical or circuit ground, the ground having a defined ground voltage;
   d) detecting a sensed voltage resulting from the excitation voltage applied to the first electrode by means of a series resistance;
   e) determining one or more rates of change in the sensed voltage per time interval, such rate or rates representing the transient immitivity response of the fluid; and
   f) providing the measured rate or rates representing the transient immitivity response as a digital or analog output.

19. A method as recited in claim 18 wherein the first and second defined voltage levels are alternately applied to the first electrode for specific time periods.

20. A method as recited in claim 18 wherein the series resistance is zero.

21. A method as recited in claim 18 wherein the sensed voltage is proportional to the electrical charges conducted through the fluid from the first electrode to the second electrode as a consequence of the excitation voltage applied to the first electrode.

22. A method as recited in claim 18 wherein the detecting step is carried out with a high input resistance to minimize external current flows.

23. A method for obtaining a transient immitivity response, comprising the steps of:
   a) contacting a fluid with a first and a second electrode, the first and second electrode being spaced apart from each other;
   b) providing a time varying excitation voltage to the first electrode, the excitation voltage being switched between a first defined voltage level and a distinct second defined voltage level, the first and second defined voltage levels being alternately applied to the first electrode for specific time periods;
   c) providing a capacitance in contact between the second electrode and an electrical or circuit ground, the ground having a defined ground voltage;
   d) detecting a sensed voltage as a consequence of the excitation voltage applied to the first electrode, wherein the detecting step is carried out with a high input resistance to minimize external current flows;
   e) determining a rate or rates of the change in the sensed voltage per time interval or intervals, such rates representing the transient immitivity response of the fluid; and
   f) providing the transient immitivity response of the fluid as a digital or analog output.

24. A method for differentiating between fluids having different dielectric constants, comprising the steps of:
   a) contacting a fluid with a first and a second electrode, the first and second electrode being spaced apart from each other;
   b) providing a time varying excitation voltage to the first electrode, the excitation voltage being switched between a first defined voltage level and a distinct second defined voltage level, the first and second defined voltage levels being alternately applied to the first electrode for specific time periods;
   c) providing a capacitance in contact between the second electrode and an electrical or circuit ground, the ground having a defined ground voltage;
   d) detecting a sensed voltage proportional to electrical charges conducted through the fluid from the first electrode to the second electrode due to the excitation voltage applied to the first electrode, wherein the detecting step is carried out with a high input resistance to minimize external current flows;
   e) repeating steps a–d) so that two or more transient immitivity response measurements are obtained, wherein each measurement is determined using a different value of series resistance applied to the excitation voltages; and
   f) providing rates of change in transient immitivity responses between the two or more measurements as a digital or analog output.

25. A method as recited in claim 24 wherein one of the measurements is made with a series resistance value of zero.

26. A method for measuring transient immitivity response, comprising the steps of:
   a) contacting a fluid with a first and a second electrode, the first and second electrode being spaced apart from each other;
   b) providing a time varying excitation voltage to the first electrode, the excitation voltage being switched between a first defined voltage level and a distinct second defined voltage level, the first and second defined voltage levels being alternately applied to the first electrode for specific time periods;
   c) providing a variable resistance between the excitation voltage and the first electrode, the resistance responsive to temperature changes in the fluid;
   d) providing a capacitance in contact between the second electrode and an electrical or circuit ground, the ground having a defined ground voltage;
   e) detecting a sensed voltage proportional to electrical charges conducted through the fluid from the first electrode to the second electrode as a consequence of the excitation voltage applied to the first electrode, wherein the detecting step is carried out with a high input resistance to minimize external current flows;
   f) determining at least one rate of change in sensed voltage per time interval, such at least one rate representing the transient immitivity response of the fluid; and
   g) providing the transient immitivity response as a digital or analog output.

* * * * *